(12) United States Patent
Bergandt et al.

(10) Patent No.: US 8,323,626 B2
(45) Date of Patent: *Dec. 4, 2012

(54) LUSTROUS AND SCRATCH-RESISTANT NAIL VARNISH THROUGH ADDITION OF SILANES

(75) Inventors: Heike Bergandt, Marl (DE); Frank Weinelt, Billerbeck (DE)

(73) Assignee: Evonik Degussa GmbH, Essen (DE)

( * ) Notice: Subject to any disclaimer, the term of this patent is extended or adjusted under 35 U.S.C. 154(b) by 106 days.

This patent is subject to a terminal disclaimer.

(21) Appl. No.: 12/036,580

(22) Filed: Feb. 25, 2008

(65) Prior Publication Data

US 2008/0206174 A1 Aug. 28, 2008

(30) Foreign Application Priority Data

Feb. 26, 2007 (DE) .......................... 10 2007 009 589

(51) Int. Cl.
*A61K 8/25* (2006.01)
*A61Q 3/02* (2006.01)

(52) U.S. Cl. ........................................................ 424/61

(58) Field of Classification Search ........................ None
See application file for complete search history.

(56) References Cited

U.S. PATENT DOCUMENTS

| | | | |
|---|---|---|---|
| 5,948,419 A * | 9/1999 | Bankert et al. ................. | 424/401 |
| 6,737,047 B2 * | 5/2004 | Jeanne-Rose et al. .......... | 424/61 |
| 6,811,856 B2 | 11/2004 | Nun et al. | |
| 6,852,389 B2 | 2/2005 | Nun et al. | |
| 6,858,284 B2 | 2/2005 | Nun et al. | |
| 7,083,828 B2 | 8/2006 | Muller et al. | |
| 7,235,298 B2 | 6/2007 | Katusic et al. | |
| 7,374,743 B2 | 5/2008 | Katusic et al. | |
| 7,399,353 B2 | 7/2008 | Nun et al. | |
| 2004/0154106 A1 | 8/2004 | Oles et al. | |
| 2005/0112326 A1 | 5/2005 | Nun et al. | |
| 2005/0118911 A1 | 6/2005 | Oles et al. | |
| 2005/0163951 A1 | 7/2005 | Oles et al. | |
| 2005/0167877 A1 | 8/2005 | Nun et al. | |
| 2005/0205830 A1 | 9/2005 | Oles et al. | |
| 2005/0208269 A1 | 9/2005 | Nun et al. | |
| 2005/0227045 A1 | 10/2005 | Oles et al. | |
| 2005/0253302 A1 | 11/2005 | Nun et al. | |
| 2006/0222815 A1 | 10/2006 | Oles et al. | |
| 2006/0235143 A1 | 10/2006 | Muller et al. | |
| 2007/0014970 A1 | 1/2007 | Nun et al. | |
| 2007/0254178 A1 | 11/2007 | Nun | |
| 2008/0084686 A1 | 4/2008 | Gutsch et al. | |
| 2008/0233063 A1 * | 9/2008 | Bergandt et al. ................. | 424/61 |
| 2008/0261032 A1 | 10/2008 | Nun et al. | |
| 2008/0280148 A1 | 11/2008 | Nun et al. | |
| 2008/0292799 A1 | 11/2008 | Nun et al. | |
| 2010/0226869 A1 | 9/2010 | Bergandt et al. | |
| 2011/0177350 A1 | 7/2011 | Bergandt et al. | |

FOREIGN PATENT DOCUMENTS

WO WO2007/093239 8/2007

OTHER PUBLICATIONS

U.S. Appl. No. 12/362,921, filed Jan. 30, 2009, Weinelt, et al.
U.S. Appl. No. 12/300,054, filed Nov. 7, 2008, Bergandt, et al.

* cited by examiner

*Primary Examiner* — Ernst Arnold
*Assistant Examiner* — Christopher R Lea
(74) *Attorney, Agent, or Firm* — Oblon, Spivak, McClelland, Maier & Neustadt, L.L.P.

(57) ABSTRACT

A nail varnish additive contains a) at least one silane of the general formula

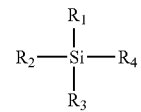

wherein the radicals $R_1$, $R_2$, $R_3$, $R_4$ are identical or different, have 1 to 40 carbon atoms and are non-crosslinking, and optionally b) at least one solvent.

10 Claims, No Drawings

LUSTROUS AND SCRATCH-RESISTANT NAIL VARNISH THROUGH ADDITION OF SILANES

BACKGROUND OF THE INVENTION

1. Field of the Invention

The present invention relates an additive for improving the properties of nail varnishes, to a process for producing such an additive, and to its use in nail varnishes.

2. Discussion of the Background

A modern nail varnish serves to maintain and convey a pleasing shape and colouration of fingernails and toenails. Additionally, the nail is protected against environmental influences and gains high hardness. Special efforts are undertaken to make applied nail varnishes long-lasting, scratch-resistant, splinterproof, in an attractive colour and pleasing lustre.

Current nail varnishes comprise a large number of ingredients. The most important representatives of these include the film formers, adhesion promoters, plasticizers, solvents and pigments. Fumed silicas are used for modifying the rheology and thixotropy. Despite this wide possibility of formulating very good varnishes, the shelf-life, hardness and scratch resistance are still unsatisfactory.

Even nowadays the primary film former used is still primarily nitrocellulose, which essentially ensures good hardness and toughness of the varnish surface. However, as is disclosed in DE 32 43 291 A1, further resins generally have to be added in order to reduce fracture and chipping.

U.S. Pat. No. 4,873,077, GB 1177420 and DE 69111621 disclose various additives for improving the wear resistance, combating splitting of the nail, avoiding cracking, chipping and fracture in the form of synthetic, natural and mineral fibres.

In the specification DE 4334938 A1, alkyl-branched and polyglycol-ether-containing fatty acid esters are recommended for rapid drying with hard and more scratch-resistant films.

For improving the external appearance, the application DE 198 22 722 A1 discloses inorganic-organic hybrid polymers which can be added to a nail varnish formulation. These are organofunctional silanes which carry three condensable and hydrolysable functions on the silicon atom, and also have a crosslinkable organic radical in the molecule. 40 to 50° C. are specified as particularly preferred drying temperatures. The drying time should be 2 to 20 min.

Copolymers of acrylates and methacrylates, disclosed in FR 7614430, and copolymers with polar functions, disclosed in DE 31 12 888 C2 are said to reduce brittleness of the dried nail varnish and improve its adhesion to the nail.

It is common to all these specifications that, to improve the properties of nail varnishes, a large number of substances is added to them which are admixed to the finished cosmetic product in an expensive process. In view of the sensitivity of the consumer towards side-effects, which has been increasing for a long time, it must also be observed that the customer will refrain completely from the use of nail varnishes if he has to reckon with allergy-triggering effects due to the admixed acrylate monomers in accordance with the background art.

DETAILED DESCRIPTION OF THE INVENTION

It is therefore an object of the present invention to provide an additive which can be admixed easily into the nail varnish and which overcomes the disadvantages of the background art.

Surprisingly, it has been found that the cosmetic features of the nail varnish are improved through the simple addition of a nail varnish additive which has a) at least one silane of the general formula

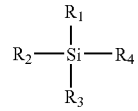

where the radicals $R_1$, $R_2$, $R_3$, $R_4$ are identical or different having 1 to 40 carbon atoms and are non-crosslinking.

The present invention therefore provides a nail varnish additive which is characterized in that the nail varnish additive has a) at least one silane of the general formula

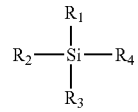

where the radicals $R_1$, $R_2$, $R_3$, $R_4$ are identical or different having 1 to 40 carbon atoms and are non-crosslinking, The present invention likewise provides a process for producing a nail varnish additive which is characterized in that a composition is produced which contains component a), or comprises these components.

The present invention likewise provides a nail varnish additive which is obtained by the process according to the invention.

In the context of the present invention, "non-crosslinking" means that the radicals $R_1$, $R_2$, $R_3$, $R_4$ are not or do not have any reactive groups (such as double bonds) which could react with themselves or other groups to build a network. "Crosslinking" in the examples below means that at least some of the radicals $R_1$, $R_2$, $R_3$, $R_4$ are converted into silanol groups which then react with other silanol groups to form a crosslinked structure.

The present invention has the advantage that the nail varnish admixed with the nail varnish additive according to the invention dries to give a highly lustrous and brilliant coating on the nail. The drying time of the nail varnish admixed with the nail varnish additive according to the invention is comparable with the drying time of the background art nail varnishes. The nail varnish additive according to the invention has the advantage that, during hardening, the silane or silanes following application to the nail surface reacts/react with the moisture available in the air with hydrolysis and condensation. For the user there is the further advantage that the nail varnish with the nail varnish additive according to the invention can be applied to the nails without its user being required to readapt, for example in the sense of longer waiting times or special application techniques out of the ordinary.

Besides rapid drying, adhesion to the nail and the ability to be removed from the nail surface is a critical product property. Comparative tests with nail varnish according to the background art have surprisingly shown that the varnish provided with the nail varnish additive according to the invention adheres just as well as or better to the surface and nevertheless can be removed using conventional nail varnish remover just as easily and rapidly as dried nail varnish according to the background art.

A particular advantage of the nail varnish additive according to the invention is to be regarded as the fact that the nail varnishes admixed therewith have higher hardness and better scratch resistance than nail varnish according to the background art. Furthermore, besides the high hardness, a certain flexibility of the varnished nail surface is also important in order to allow movements of the nail with it and thereby to have the lowest possible tendency for chipping and fracture. Nail varnish admixed with nail varnish additive according to the invention has the advantage that the dried nail varnish, compared with the background art, chips or fractures less, if at all.

The present invention therefore also provides the use of the nail varnish additive according to the invention in a nail varnish.

Furthermore, an advantage of the present invention is that the proportion of film-forming components such as nitrocellulose and/or polyacrylates, which can have an allergic sensitizing effect, in the nail varnish can be reduced as a result of adding the silane or the silanes or such film-forming components can be dispensed with entirely. If the performance profile even of a conventional nail varnish is significantly improved as a result of adding the nail varnish additive according to the invention, one advantage of the present invention being that no undesired competing reactions of any kind with the components according to the background art arise, it is a very particular advantage of the present invention that the proportion of these components with which hardness, lustre, flexibility and scratch resistance of the conventional nail varnish are usually achieved in the art can be reduced. Hardness, lustre, brilliance, flexibility and scratch resistance are achieved merely as a result of adding the nail varnish additive according to the invention in the nail varnish provided therewith and even improved compared with the features of conventional nail varnishes.

The present invention therefore likewise provides a nail varnish which contains or is the nail varnish additive according to the invention which hardens following application to the nail as a result of reaction with atmospheric moisture. The present invention therefore also further provides the use of the nail varnish according to the invention for cosmetics and/or nail care.

The nail varnish according to the invention has the advantage of better protecting the nail against impacts and environmental influences as result of the simultaneously improved flexibility and hardness. Fracture and chipping of the nails are likewise advantageously reduced.

The present invention is described below by reference to an example without any intention to restrict the invention, the protective scope of which arises from the claims and the description, thereto. The claims themselves also belong to the disclosure content of the present invention. Where the text below states ranges or preferred ranges, then all theoretically possible part ranges within these ranges should also belong to the disclosure content of the present invention without these having been explicitly specified for reasons of better clarity.

The present invention provides a nail varnish additive, characterized in that the nail varnish additive has a) at least one silane of the general formula

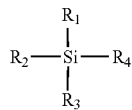

where the radicals $R_1$, $R_2$, $R_3$, $R_4$ are identical or different having 1 to 40 carbon atoms and are non-crosslinking.

It may be advantageous if the radicals $R_1$, $R_2$, $R_3$, $R_4$ of component a) of the nail varnish additive according to the invention are selected from straight-chain, branched or alicyclic alkyl, fluoroalkyl, aryl, alkoxy groups, or a combination of these groups. Particular preference is given to selecting alkoxy groups. Preferably, the alkoxy groups of the nail varnish additive according to the invention can be selected from methoxy, ethoxy, propoxy, butoxy, particularly preferably selected from ethoxy, methoxy, propoxy, very particularly preferably ethoxy, methoxy, or a combination of these groups.

It may furthermore be advantageous if the nail varnish additive according to the invention has a further component b) at least one solvent.

Preferably, component b) of the nail varnish additive according to the invention can be selected from the series of alcohols of the general formula $C_nH_{2n+1}OH$, where n=1 to 4, particularly preferably n=2 or 3, from the series of polyhydric alcohols, from ketones, acetates, glycol ethers, toluene, xylene, or from a mixture of these solvents. This component can particularly preferably be selected from glycols, acetone, methyl ethyl ketone, ethyl acetate, butyl acetate, ethylene glycol monomethyl ether, or a mixture of these solvents.

The present invention likewise provides a process for producing a nail varnish additive, characterized in that a composition is produced which contains component a), or comprises these components.

It may be advantageous if in the process according to the invention a composition is produced which contains the further component b) in an amount from 0 to 50% by weight, the quantitative data being based in each case on the composition, and with the proviso that the sum of the weight fractions is 100%.

Preferably, in the process according to the invention, a composition is produced which contains component a), or comprises these components in an amount from 0.01 to 99.9% by weight, preferably from 1 to 95% by weight, more preferably from 2 to 90% by weight, particularly preferably from 5 to 75% by weight, more particularly preferably from 10 to 70% by weight, further particularly preferably from 15 to 68% by weight, very particularly preferably from 25 to 65% by weight, and component b) in an amount from 0.01 to 49.9% by weight, preferably from 1 to 45% by weight, more preferably from 2 to 40% by weight, particularly preferably from 5 to 35% by weight, more particularly preferably from 8 to 38% by weight, very particularly preferably from 10 to 35% by weight, the quantitative data being based in each case on the composition, and with the proviso that the sum of the weight fractions is 100%.

It may be advantageous if, in the process according to the invention, components a) and b) are mixed by stirring. In the process according to the invention, the components can be particularly preferably mixed together by stirring in a propeller stirrer, oblique-blade stirrer, disc stirrer, impeller stirrer, cross-blade stirrer, anchor stirrer, blade stirrer, gate stirrer, helical stirrer, toothed-disc stirrer, turbine stirrer, half-moon stirrer, or fan stirrer. It may be advantageous if, in the process according to the invention, stirring techniques are used which introduce little or no ambient gas into the composition and/or in which little heat energy is introduced into the composition. In the process according to the invention, propeller stirrers, oblique-blade stirrers, disc stirrers, impeller stirrers, cross-blade stirrers, anchor stirrers, blade stirrers, gate stirrers, helical stirrers, or toothed-disc stirrers can be used very particularly preferably, furthermore propeller stirrers, disc stirrers or impeller stirrers can be used very particularly preferably.

Preferably, in the process according to the invention, components b) and a) can be mixed together with low shear rates over a period of from 1 to 10 min, preferably from 2 to 8 min, particularly preferably from 3 to 7 min, very particularly preferably from 4 to 6 min, extraordinarily particularly preferably from 4.8 to 5.2 min.

It may furthermore be advantageous if, in the process according to the invention, the solvent is initially introduced and then component a) is added thereto with stirring. Preferably, in the process according to the invention, component b) and a) can be mixed at a temperature from 1 to 30° C., particularly preferably from 5 to 28° C., further particularly preferably from 10 to 25° C., very particularly preferably from 18 to 21.5° C., extraordinarily preferably at room temperature by stirring.

The present invention likewise provides the use of the nail varnish additive according to the invention in a nail varnish.

It may be advantageous if the nail varnish additive according to the invention is used in a concentration from 1 to 13% by weight, preferably from 1.5 to 12% by weight, particularly preferably from 2 to 11% by weight, very particularly preferably from 2.5 to 10% by weight, in the nail varnish. For the purposes of the present invention, the weight data are based on the weight of the nail varnish ready for the user and prepared for application to the nails. In one advantageous embodiment of the use according to the invention, the nail varnish additive according to the invention can be incorporated into this nail varnish by stirring or shaking with the nail varnish, which may be a conventional nail varnish or a nail varnish without film-forming components. The use according to the invention has the advantage that the dried nail varnish applied to the nail simultaneously has luster, brilliance, hardness, wear resistance and flexibility. If preferably as component a) Dynasylan A, Dynasylan TEOS, Dynasilan MTES, all of these silanes available from Degussa GmbH, Paul-Baumann-Strasse 1, 45764 Marl, trimethylethoxysilane, phenylethyltriethoxysilane, or a mixture of these silanes is used, the use according to the invention furthermore has the advantage that the resulting nail varnish retains the cosmetically intended shade, compared with the shade of conventional nail varnish, meaning that reformulation with regard to the color design is not necessary.

The nail varnish additive according to the invention is illustrated in more detail below by reference to a number of examples, without intending to restrict the invention to these embodiments.

EXAMPLES

Example 1

Preparation of a Nail Varnish Additive 30 g of Dynasylan TEOS and 30 g of butyl acetate were mixed together at room temperature in a propeller stirrer for a period of 5 min.

10% by weight of the nail varnish additive obtained in this way was then added to 90% by weight of standard commercial nail varnish. The nail varnish additive was mixed thoroughly with the nail varnish by stirring at room temperature until a homogeneous distribution was achieved.

Drying of the nail varnish was accompanied by crosslinking and condensation of the silane following application of the nail varnish to the nail surface as a result of the reaction with atmospheric moisture.

Example 2

As Example 1, but using 45 g of Dynasylan TEOS and 55 g of Dynasylan MTES as nail varnish additive.

Example 3

As Example 1, but using 20 g of trimethylethoxysilane, 50 g of Dynasylen TEOS, 10 g of Dynasylan MTES and 20 g of isopropanol as nail varnish additive.

Example 4

As Example 2, but mixing 5% by weight of nail varnish additive with 95% by weight of standard commercial nail varnish.

Example 5

As Example 3, but mixing 2.5% by weight of nail varnish additive with 97.5% by weight of standard commercial nail varnish.

Example 6

As Example 1, but mixing the nail varnish additive with a non-conventional nail varnish. The non-conventional nail varnish had the composition according to Table 1.

TABLE 1

| | |
|---|---|
| 16 g | Nitrocellulose obtained from Wolff Cellulosics GmbH & Co. KG |
| 10 g | Arylsulphonamide |
| 6 g | Acetyl tributylcitrate, camphor |
| 1.5 g | Stearalkonium bentonite |
| 1.5 g | Pigments |
| 65 g | Butyl acetate |

Example 7

As Example 1, but mixing the nail varnish additive with a non-conventional nail varnish. The non-conventional nail varnish had the composition according to Table 2.

TABLE 2

| | |
|---|---|
| 16.5 g | Nitrocellulose (Wolff Cellulosics GmbH & Co. KG) |
| 10.3 g | Arylsulphonamide |
| 6.2 g | Acetyl tributylcitrate, camphor |
| 67 g | Butyl acetate |

Example 8

As Example 1, but mixing the nail varnish additive with a non-conventional nail varnish. The non-conventional nail varnish had the composition according to Table 3.

TABLE 3

| | |
|---|---|
| 10 g | Nitrocellulose (Wolff Cellulosics GmbH & Co. KG) |
| 6 g | Styrene/acrylate copolymer |
| 3 g | Silane mixture from Example 1 |
| 6 g | Acetyl tributylcitrate, camphor |
| 1.5 g | Stearalkonium bentonite |
| 1.5 g | Pigments |
| 36 g | Butyl acetate |
| 36 g | Ethyl acetate |

Example 9

As Example 1, but mixing the nail varnish additive with a non-conventional nail varnish. The non-conventional nail varnish had the composition according to Table 4.

TABLE 4

| | |
|---|---|
| 16 g | Nitrocellulose (Wolff Cellulosics GmbH & Co. KG) |
| 6 g | Styrene/acrylate copolymer |
| 3.0 g | Silane mixture from Example 2 |
| 6.2 g | Acetyl tributylcitrate, camphor |
| 40 g | Butyl acetate |
| 28.3 g | Ethyl acetate |

Example 10

As Example 1, but mixing the nail varnish additive with a non-conventional nail varnish. The non-conventional nail varnish had the composition according to Table 5.

TABLE 5

| | |
|---|---|
| 15.0 g | Nitrocellulose (Wolff Cellulosics GmbH & Co. KG) |
| 9.5 g | Arylsulfonamide |
| 3.0 g | Silane mixture from Example 3 |
| 5.7 g | Acetyl tributylcitrate, camphor |
| 1.4 g | Stearalkonium bentonite |
| 1.4 g | Pigments |
| 64.0 g | Butyl acetate |

Example 11

As Example 1, but mixing the nail varnish additive with a non-conventional nail varnish. The non-conventional nail varnish had the composition according to Table 6.

TABLE 6

| | |
|---|---|
| 15.7 g | Nitrocellulose (Wolff Cellulosics GmbH & Co. KG) |
| 9.8 g | Arylsulfonamide |
| 2.5 g | Silane mixture from Example 1 |
| 5.9 g | Acetyl tributylcitrate, camphor |
| 66.1 g | Butyl acetate |

German patent application 10 2007 009 589.0 filed Feb. 26, 2007, is incorporated herein by reference.

Numerous modifications and variations on the present invention are possible in light of the above teachings. It is therefore to be understood that within the scope of the appended claims, the invention may be practiced otherwise than as specifically described herein.

The invention claimed is:

1. A nail varnish additive, comprising:
   a)
      (a1) tetraethoxysilane in an amount of 45% by weight of component a), and
      (a2) methyl triethoxy silane in an amount of 55% by weight of component a), wherein the silanes (a1) and (a2) are comprised in the additive in an amount ranging from 50% to 100% by weight, based on the total weight of the additive.

2. The nail varnish additive according to claim 1, further comprising:
   b) at least one solvent in an amount ranging from a positive amount greater than 0% to 50% by weight, based on the weight of the composition.

3. The nail varnish additive according to claim 2, wherein component b) is selected from the group consisting of at least one alcohol of the general formula $C_nH_{2n+1}OH$, wherein n=1 to 4, a mixture of alcohols of the general formula $C_nH_{2n+1}OH$, wherein n=1 to 4, a polyhydric alcohol, a ketone, an acetate, a glycol ether, toluene, xylene, and mixtures thereof.

4. A nail varnish, comprising:
   the nail varnish additive according to claim 1.

5. The nail varnish according to claim 4, which hardens following application to a nail by reaction with the moisture in the air.

6. A nail varnish comprising the nail varnish additive of claim 2.

7. A nail varnish comprising the nail varnish additive of claim 3.

8. A process for producing the nail varnish additive of claim 1, the process comprising:
   combining
   a)
      (a1) tetraethoxysilane, and
      (a2) methyl triethoxy silane.

9. The process according to claim 8, wherein the process further comprises combining, with silanes (a1) and (a2),
   b) at least one solvent in an amount ranging from a positive amount greater than 0% to 50% by weight, based on the weight of the composition.

10. The process according to claim 9, wherein the combining is effected by stirring.

* * * * *